United States Patent [19]

Guadagno et al.

[11] Patent Number: 5,196,167

[45] Date of Patent: Mar. 23, 1993

[54] FECAL OCCULT BLOOD TEST PRODUCT WITH POSITIVE AND NEGATIVE CONTROLS

[75] Inventors: Philip A. Guadagno, Vidor; Janine P. Burrows, Orange, both of Tex.

[73] Assignee: Helena Laboratories Corporation, Beaumont, Tex.

[21] Appl. No.: 697,419

[22] Filed: May 9, 1991

Related U.S. Application Data

[62] Division of Ser. No. 333,828, Apr. 4, 1989.

[51] Int. Cl.$^5$ ............................................. G01N 33/48
[52] U.S. Cl. ...................................... 422/56; 422/57; 422/58; 422/61; 436/66; 436/169
[58] Field of Search ..................... 422/56, 57, 58, 61; 436/66, 169

[56] References Cited

U.S. PATENT DOCUMENTS

| | | | |
|---|---|---|---|
| Re. 28,575 | 10/1975 | Bauer | 435/28 |
| 2,223,520 | 12/1940 | Ioannu | 435/93 |
| 2,290,436 | 7/1942 | Kamlet | 436/66 |
| 2,387,244 | 10/1945 | Compton et al. | 436/95 |
| 2,394,140 | 2/1946 | Biscow | 606/119 |
| 2,418,392 | 4/1947 | Bender | 206/0.5 |
| 2,567,445 | 9/1951 | Parker | 436/20 |
| 2,754,289 | 7/1956 | Meyer | 526/68 |
| 2,773,906 | 12/1956 | Emerson | 568/573 |
| 2,799,660 | 7/1957 | Nicholls et al. | 436/66 |
| 2,800,457 | 7/1957 | Green et al. | 428/402.2 |
| 2,800,458 | 7/1957 | Green | 428/402.2 |
| 2,823,984 | 2/1958 | Mavrodineanu | 436/124 |
| 2,838,377 | 6/1958 | Fonner | 436/66 |
| 2,848,308 | 8/1958 | Free | 435/14 |
| 2,886,445 | 5/1959 | Rosenthal et al. | 426/5 |
| 2,893,844 | 7/1959 | Cook | 435/14 |
| 2,905,594 | 9/1959 | Morris | 435/28 |
| 2,930,695 | 3/1960 | Rosner et al. | 514/734 |
| 2,953,454 | 9/1960 | Berman | 430/345 |
| 2,986,453 | 5/1961 | Collins | 422/56 |
| 3,012,976 | 12/1961 | Adams, Jr. et al. | 436/66 |
| 3,017,879 | 1/1962 | Sapit et al. | 128/636 |
| 3,034,922 | 5/1962 | Boë et al. | 162/100 |
| 3,042,496 | 7/1962 | Fancher et al. | 435/14 |
| 3,043,782 | 7/1962 | Jensen | 427/213.35 |
| 3,057,723 | 10/1962 | Jeffreys et al. | 430/449 |
| 3,066,081 | 11/1962 | Rorem et al. | 435/14 |
| 3,092,463 | 6/1963 | Adams, Jr. et al. | 422/56 |
| 3,092,464 | 6/1963 | Adams, Jr. et al. | 422/56 |
| 3,116,223 | 12/1963 | Rosner et al. | 435/14 |
| 3,183,173 | 5/1965 | Oakes | 435/10 |
| 3,232,710 | 2/1966 | Rieckmann et al. | 435/25 |
| 3,252,762 | 5/1966 | Adams, Jr. et al. | 422/56 |
| 3,290,117 | 12/1966 | Adams, Jr. et al. | 422/56 |
| 3,293,683 | 12/1966 | Wyant | 15/104.93 |
| 3,350,278 | 10/1967 | Gretton et al. | 435/14 |
| 3,406,015 | 10/1968 | Foster | 435/28 |
| 3,406,106 | 10/1968 | Garwood et al. | 205/203 |
| 3,411,887 | 11/1968 | Chiu-Choon Ku | 435/8 |
| 3,418,079 | 12/1968 | Rey et al. | 422/56 |
| 3,438,737 | 4/1969 | Atkinson et al. | 436/86 |
| 3,443,903 | 5/1969 | Haack et al. | 436/169 |
| 3,447,536 | 6/1969 | Snyder | 604/348 |

(List continued on next page.)

FOREIGN PATENT DOCUMENTS 093595 11/1983 European Pat. Off. .
047359 2/1972 Japan .
1018563 1/1966 United Kingdom .

Primary Examiner—Robert J. Warden
Assistant Examiner—Laura E. Collins
Attorney, Agent, or Firm—Spencer, Frank & Schneider

[57] ABSTRACT

A test sheet for the determination of the presence of a substance having peroxidase-like activity in a throw-in-the-bowl fecal occult blood test, includes a specimen test area and a positive control area. The test area has deposited thereon a test ink having at least one oxygen donor reagent and a chromogen reagent capable of being oxidized by the oxygen donor in the presence of blood or a substance having peroxidase-like activity, to provide a visually observable change of color. The test ink also includes a water soluble polymer for immobilizing the chromogen and oxygen donor. The positive control area has deposited thereon the test ink and a substance having the peroxidase-like activity.

16 Claims, 1 Drawing Sheet

U.S. PATENT DOCUMENTS

| | | | |
|---|---|---|---|
| 3,453,180 | 7/1969 | Fraser, Jr. et al. | 435/14 |
| 3,466,145 | 9/1969 | Duyne | 422/103 |
| 3,472,738 | 10/1969 | Foster | 422/56 |
| 3,507,269 | 4/1970 | Berry | 128/636 |
| 3,509,872 | 5/1970 | Truhan | 128/771 |
| 3,511,608 | 5/1970 | Anderson | 422/56 |
| 3,526,480 | 9/1970 | Findl et al. | 422/66 |
| 3,552,925 | 1/1971 | Fetter | 436/169 |
| 3,558,435 | 1/1971 | Rey et al. | 435/14 |
| 3,598,704 | 8/1971 | Dablqvist | 435/14 |
| 3,625,654 | 12/1971 | Duyne | 422/102 |
| 3,627,697 | 12/1971 | Rey et al. | 436/165 |
| 3,627,698 | 12/1971 | Rey et al. | 436/135 |
| 3,630,847 | 12/1971 | Rey et al. | 435/14 |
| 3,630,957 | 12/1971 | Rey et al. | 436/66 |
| 3,654,179 | 4/1972 | Bauer | 435/28 |
| 3,654,180 | 4/1972 | Bauer | 435/28 |
| 3,668,076 | 6/1972 | Rey et al. | 435/28 |
| 3,672,351 | 6/1972 | Ubersax et al. | 128/638 |
| 3,699,005 | 10/1972 | Foster | 435/21 |
| 3,712,853 | 1/1973 | Rittersdorf et al. | 435/37 |
| 3,713,772 | 1/1973 | Tavel | 435/14 |
| 3,811,840 | 5/1974 | Bauer et al. | 422/56 |
| 3,814,668 | 6/1974 | Blake et al. | 435/14 |
| 3,847,553 | 11/1974 | Verbeck | 422/56 |
| 3,853,468 | 12/1974 | Haymond | 436/531 |
| 3,853,471 | 12/1974 | Rittersdorf et al. | 436/66 |
| 3,853,472 | 12/1974 | Rittersdorf et al. | 436/66 |
| 3,854,885 | 12/1974 | Fromm et al. | 422/86 |
| 3,912,457 | 10/1975 | Ogawa et al. | 422/56 |
| 3,917,452 | 11/1975 | Rittersdorf et al. | 436/66 |
| 3,964,871 | 6/1976 | Hochstrasser | 435/10 |
| 3,975,161 | 8/1976 | Svoboda et al. | 422/56 |
| 3,986,833 | 10/1976 | Mast et al. | 422/55 |
| 3,996,006 | 12/1976 | Pagano | 422/50 |
| 4,005,984 | 2/1977 | Alsop | 436/66 |
| 4,017,261 | 4/1977 | Svoboda et al. | 422/56 |
| 4,035,150 | 7/1977 | Jaffe | 436/66 |
| 4,046,514 | 9/1977 | Johnston et al. | 422/56 |
| 4,061,468 | 12/1977 | Lange et al. | 422/56 |
| 4,063,894 | 12/1977 | Ogawa et al. | 436/66 |
| 4,071,318 | 1/1978 | Lam | 422/56 |
| 4,092,120 | 5/1978 | Suovaniemi et al. | 422/56 |
| 4,148,611 | 4/1979 | Nand et al. | 436/66 |
| 4,175,923 | 11/1979 | Friend | 436/66 |
| 4,219,336 | 8/1980 | Guthlein et al. | 436/66 |
| 4,220,713 | 9/1980 | Rittersdorf et al. | 435/14 |
| 4,251,222 | 2/1981 | White | 431/215 |
| 4,251,223 | 2/1981 | White | 436/66 |
| 4,260,393 | 4/1981 | Gibson | 436/66 |
| 4,269,938 | 5/1981 | Frank | 435/7.9 |
| 4,277,250 | 7/1981 | Melnick et al. | 436/66 |
| 4,278,439 | 7/1981 | White | 436/66 |
| 4,292,272 | 9/1981 | Kitajima et al. | 422/57 |
| 4,303,409 | 12/1981 | Ogawa et al. | 436/93 |
| 4,310,626 | 1/1982 | Burkhardt et al. | 435/28 |
| 4,329,317 | 5/1982 | Detweiler et al. | 422/58 |
| 4,333,734 | 6/1982 | Fleisher | 436/66 |
| 4,365,970 | 12/1982 | Lawrence et al. | 422/56 |
| 4,385,114 | 5/1983 | Güthlein et al. | 436/95 |
| 4,447,542 | 5/1984 | Gantzer | 436/66 |
| 4,486,536 | 12/1984 | Baker et al. | 436/66 |
| 4,493,892 | 1/1985 | Fleisher | 435/28 |
| 4,511,533 | 4/1985 | Guadagno | 422/61 |
| 4,541,987 | 9/1985 | Guadagno | 422/56 |
| 4,556,640 | 12/1985 | Gantzer | 436/66 |
| 4,578,358 | 3/1986 | Oksman et al. | 436/66 |
| 4,725,553 | 2/1988 | Guadagno | 436/66 |
| 4,742,002 | 5/1988 | Guadagno et al. | 435/28 |
| 4,743,559 | 5/1988 | Koevér et al. | 422/56 |
| 4,755,472 | 7/1988 | Ismail et al. | 422/56 |
| 4,803,171 | 2/1989 | Baier et al. | 422/56 |

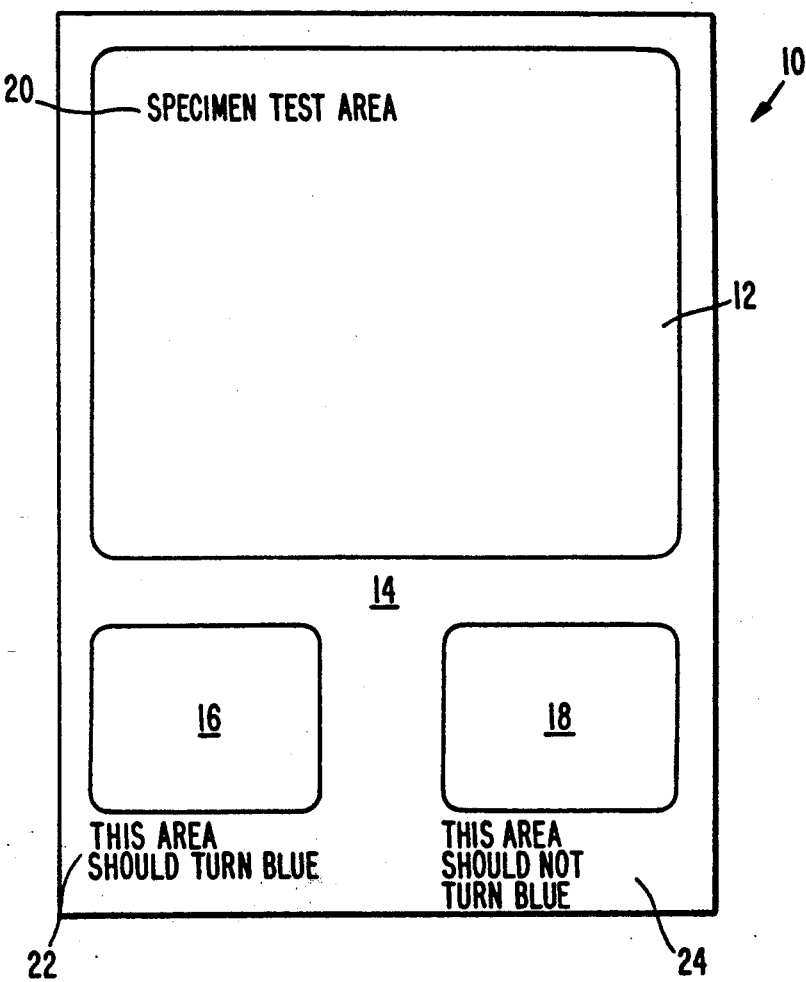

FECAL OCCULT BLOOD TEST PRODUCT WITH POSITIVE AND NEGATIVE CONTROLS

CROSS-REFERENCE TO RELATED APPLICATION

This application is a division of application Ser. No. 07/333,828 filed Apr. 4, 1989. This application is related to the copending application of Patel, et al., application Ser. No. 07/363,457 filed Jun. 6, 1989, now U.S. Pat. No. 5,081,040, which is in turn a continuation of application Ser. No. 07/068,745 filed Jun. 29, 1987, now abandoned, which in turn is a continuation of application Ser. No. 06/888240 filed Jun. 21, 1986, now abandoned, all of which are owned by the Assignee of this application. The aforementioned Patel, et al. applications are prior art to this application.

BACKGROUND OF THE INVENTION

The present invention relates generally to an occult blood test product, of the type to be physically placed into a toilet bowl containing a fecal specimen, for detecting the presence of fecal occult blood in an aqueous solution. More particularly, the present invention relates to an improved, reliable fecal occult blood test product which may be utilized with a minimum of human intervention. The principles of the present invention may be employed in the testing for occult blood, ferritin and myoglobin in various biological fluids.

In general terms, the testing of a fecal specimen for occult blood is based on the well-known principle that blood (more particularly hemoglobin) will function as a catalyst and cause oxygen to be liberated from an oxygen donor, with the liberated oxygen thus causing a color change in a chromogenic substance. As such, the test for fecal occult blood is not only well-known, but numerous oxygen donors, numerous chromogens and numerous donor-chromogen pairs have been suggested in the prior literature. In considering the chromogens and oxygen donors which may be used, it should be appreciated that the fecal occult blood test is frequently referred to as a test for the presence of a substance having a peroxidase-like activity.

In addition, there are several principle styles of fecal occult blood test products which have been marketed or described in the literatures. These include slides, tape, wipe and throw-in-the-bowl products. Slide products require the patient to retrieve part of the stool specimen and, using a spatula or equivalent device, place part of the specimen on a paper which paper is thereafter submitted to a laboratory where a developing solution is applied to the slide. Tape products are typically utilized by a physician after a rectal examination in which instance the physician smears a stool sample on a thin, narrow tape and then a developing solution is applied to the tape. In both of these types of products, the chromogen is guaiac, and the oxygen donor or developing solution is hydrogen peroxide.

A third type of product is often referred to as the wipe type of product where a form of toilet paper is impregnated with a suitable chemical, typically the chromogen and after a bowel movement, the patient self-wipes the anal area, and thereafter may apply the developing solution to the paper. As may be appreciated, in each of these types of products there is a need for the patient (or physician) to physically handle or physically contact the fecal specimen. Thus, there is a natural reluctance to employ these types of products, notwithstanding that they are well-known as beneficial screening agents, to assist in the early detection of colo-rectal cancer and other gastrointestinal disorders.

In Nov. 1979, U.S. Pat. No. 4,175,923 issued to William Friend. This patent described a fecal occult blood test product of the throw-in-the-bowl type where a guaiac impregnated sheet was sprayed with a developing solution (hydrogen peroxide) and then placed into a toilet bowl containing a fecal specimen. If blood was present, the blood catalyzed a chromogenic reaction, and a blue color was observed in the toilet bowl. The product described in the Friend patent also included a positive monitor which would turn blue if the chemicals were functioning properly. However, the product as described in the Friend patent still required patient intervention in that the patient was required to apply the developer to the test product.

Guadagno U.S. Pat. No. 4,541,987, issued Sep. 17, 1985, relates to a throw-in-the-bowl type of product which included both positive and negative test monitors. A product generally in accordance with the teachings of the Guadagno patent has been successfully marketed by Helena Laboratories Corporation, of Beaumont, Tex., under their trademark CS-T. Helena Laboratories Corporation is the Assignee of the Guadagno patent and Assignee of the instant application. The CS-T brand of fecal occult blood test product is commercially successful and medically reliable.

In addition to the CS-T brand of fecal occult blood test product, which is in the nature of a test pad or sandwich of dry chemicals between layers of paper, a thin film type of product for throw-in-the-bowl fecal occult blood testing is known as described in the aforementioned Patel, et al. applications. However, the product of the type described in the Patel, et al. applications has not met with success in the market place even though it does not require patient intervention. The product of the Patel, et al. application does not include self-contained controls or monitors, and the product as marketed has heretofore utilized an external type of positive monitor which must be dropped into the toilet bowl.

Thus, there is a need for a less expensive, reliable, easy to use throw-in-the-bowl type of fecal occult blood test product which is easy to manufacture and provides consistent, reliable results, and which also includes built-in or self-contained positive and negative monitors. These self-contained monitors, of course, aid the patient because the monitors inform the patient if a positive or a negative result should be ignored a being induced by contaminants or being the result of loss of activity by the chromogen or oxygen donor. In this fashion, a patient will know to repeat a test rather than rely upon false test results.

Hence, the present invention responds to these needs by providing an improved formulation of film-type throw-in-the-bowl fecal occult blood type product.

SUMMARY OF THE INVENTION

The present invention provides an improved test product for the determination of the presence of occult blood, which product may be placed into a toilet bowl without patient intervention as heretofore described. The test product of the present invention includes not only a specimen test area but, in addition, a positive monitor area and a negative monitor area.

The test product is, in a preferred embodiment, a sheet of filter paper upon which the chromogen and oxygen donor are printed as a test ink. Thus, the test ink includes at least one oxygen donor reagent and at least one chromogen reagent capable of undergoing a visible color change when oxygen is liberated by the oxygen donor. The test ink may include a stabilizer for preventing premature interaction between the oxygen donor and the chromogen. The test ink is printed on the test sheet in the specimen test area and in the positive monitor area but not in the negative monitor area. A polymer barrier is then printed over the test ink. Lastly, a positive monitor ink is printed in the positive monitor area, on top of the polymer barrier. The purpose of the positive monitor ink is that if the chemicals are functioning properly, then there will be a visible color change in the positive monitor area. Thus, the positive monitor ink includes a substance which will catalyze the liberation of oxygen from the oxygen donor reagent.

BRIEF DESCRIPTION OF THE DRAWING

The foregoing objects and advantages of the present invention, together with other advantages which may be attained by the principles of the present invention, will become more apparent upon reading the following detailed description of the invention in conjunction with the drawings.

In the drawings, the single Figure illustrates the test product of the present invention.

DETAILED DESCRIPTION OF THE INVENTION

The single Figure illustrates a test product or test pad 10 in accordance with the present invention. The pad 10 is illustrated as a generally rectangular sheet having a large test area 12, which may advantageously occupy approximately more than half of the surface area of the sheet, and a monitor or control region 14 which may include a positive monitor test area 16 and a negative monitor test area 18. The two monitor test areas 16, 18, are approximately equal to each other in size. Suitable legends or directions 20, 22 and 24 may be included on the test product.

The entire test pad 10, in accordance with the principles of the present invention, may be a sheet of water insoluble matrix or material such as Whatman filter paper having fibers or interstitial spaces. A suitable alternative to the Whatman filter paper would be Schleicher & Schuell No. 596 filter paper. The overall dimensions of the sheet may be 4×5 inches. The paper as described is of the short fiber type which is sufficiently water repellant for the desired purpose such that the paper does not prematurely shred when initially immersed into an aqueous solution. It should be pointed out that all dimensions and ratios of the specimen test area and monitor areas ar for illustrative purposes and should not be taken as a limitation on the present invention.

A test ink is deposited, i.e., printed on the entire sheet except the negative monitor test area 18. The printing deposits the test ink onto the test sheet, and the terms "printing" and "depositing" are used in the broad sense to include not only placing the ink on the surface of the sheet but also to include any desired degree of impregnation of the ink into the sheet. The test ink includes at least one chromogen reagent which will undergo a visible color change in the presence of liberated oxygen, and at least one oxygen donor reagent which will liberate oxygen when catalyzed by the presence of hemoglobin. It should be appreciated that the prior art literature lists or catalogs virtually hundreds of chromogens and virtually hundreds of oxygen donors, but the prior art does not necessarily indicate which chromogen-donor pairs or couples are suitable for detecting hemoglobin and which are printable and which may be suitably isolated as to preclude premature interaction as will be hereinafter described.

According to the principles of the present invention, we have discovered that a preferred chromogen is 3,3',5,5'-tetramethylbenzidine and a preferred oxygen donor is cumene hydroperoxide ($\alpha,\alpha'$-dimethylbenzyl hydroperoxide).

However, it must be appreciated that it is not satisfactory to merely determine the appropriate quantities of the above two ingredients (or the appropriate quantities of all the other ingredients) necessary to achieve the desired sensitivity, mix them together and deposit them on the test sheet. This does not assure desired sensitivity nor reproducibility of results nor reliability. Thus, it is not merely satisfactory to calculate molarities and provide suitable quantities of chromogen, oxygen donor and any other ingredients for a stoichiometrically balanced reaction. Such a procedure would produce a test composition which would function properly in the laboratory, such as in a test tube, but not necessarily be mechanically printable and not necessarily be functional under normally occurring conditions. In addition, in the system described herein, the chromogen is a solid at room temperature and must be dissolved or solubilized in a solvent which will be inert or inactive relative to the detection of hemoglobin. According to the principles of the present invention, a preferred solvent or surfactant is alkylphenoxypolyethoxyethanol which is marketed as Triton X-100 by Sigma Chemical Co.

As will be further described, the positive monitor area will contain a substance having peroxidase-like activity, preferably hemoglobin. During the manufacture of the test product and thereafter until the test product is immersed in a toilet bowl, it is important to prevent the positive monitor from catalyzing a reaction between the oxygen donor and the chromogen. For this reason, it may be desirable for the test ink to include a stabilizing agent which prevents the chromogen and oxygen donor from interacting prematurely. A suitable stabilizer is triethanolamine borate, as described in U.S. Pat. No. 4,071,318. However, the stabilizer must be encapsulated and put into solution as part of the preparation of the test ink. To accomplish this objective, the triethanolamine borate is dissolved in a foaming agent such as Stepanol AM which is distributed by the Stephan Company of Northfield, Ill. Furthermore the preferred foaming agent provides certain additional benefits such as increasing the hydrophilic nature of the test sheet.

We have further discovered that an alternative, equally satisfactory stabilizer is boron phosphate which may also be dissolved in a foaming agent. Lastly we have discovered that within the tolerances of mechanically printing the ink, and using accelerated degradation tests as described in U.S. Pat. No. 4,071,318, substantially equivalent results have been obtained without either of the above two stabilizing agents.

In addition, the test ink includes one or more water soluble polymers which encapsulate the test ink and function as a moisture barrier against ambient moisture, e.g., humidity. The moisture barrier should be solid at room temperature, and a preferred polymer is polyvinylpyrrolidone. Preferably a low molecular weight PVP may be used such as PVP 30. The PVP also tends to render the test area 12 of the sheet 10 hydrophilic, so that the test area 12 wets more readily than the unprinted negative monitor area 18.

As will be readily appreciated by those skilled in the art, the actual concentrations of the ingredients of the composition of the test ink may be varied, which will also result in varying the sensitivity of the test product 10 and the intensity of the color which develops in a positive test. Therefore, although the invention provides a distinct color reaction in response to as little as 1.5 to 2.0 mg of hemoglobin per 100 ml of test sample, for a particular application the sensitivity of the kit may be increased to be outside this sensitivity range.

It should be appreciated that the present invention relates to a fecal occult blood test product which is to be utilized by patients within the privacy of their homes Thus, the results of the use of the specimen test sheet 20 will not be interpreted by medically skilled or medically experienced personnel. For this reason, we have included yet another ingredient in the test ink, namely, a color enhancer such as 6-methoxyquinoline.

In the preparation of the test sheet, the test ink may be deposited on the sheet by various printing techniques such as using an offset press, an ink stamp pad, a flexopress, etc. Various adjustments may be made in the formulation which is hereafter described depending upon the specific printing technique employed. The formulation hereafter described is suitable for use with an offset press or a conventional ink stamp pad.

After the test ink is printed on the entire test sheet except the negative monitor area 18, then a polymer barrier is printed over the entire sheet. Thereafter, a positive monitor ink must be applied to the positive monitor test area 16. A preferred formulation for the positive monitor test ink is a 3% solution of crystalline hemoglobin in Triton X-100 which is ground on a 3 roller mill and then printed or deposited in the positive monitor area.

A test ink made according to the following example has been evaluated for sensitivity and reproducibility of results. When compared to commercially available fecal occult blood test products which have been approved by the FDA, comparable results are achieved by the following formulation.

Example of Test Ink 22.5 grams of Triton X-100;
1.0 gram of 3,3',5,5' tetramethylbenzidine;
6.0 grams of a 10% solution of triethanolamine borate in Stepanol AM, (optional) or 6.0 grams of a 10% solution of boron phosphate in Stepanol AM, (optional);
6.0 grams of Stepanol AM;
2.5 grams of a 5% solution of polyvinylpyrrolidone-30 in Triton X-100;
10.0 grams of cumene hydroperoxide; and
1.0 gram of 6-methoxyquinoline.

Method of Formulating the Test Ink

We believe that the method of formulating the test ink, i.e., the sequence of adding the ingredients, is important for a successful fecal occult blood test product. First, the chromogen is dissolved in the Triton X-100 solvent. The stabilizer, if it is to be utilized, is prepared separately, i.e., 6.0 grams of a 10% solution of either boron phosphate or triethanolamine borate in Stepanol AM. The stabilizer is then added to the chromogen. Then, the additional Stepanol AM is added. This becomes the first portion of the test ink. Then, separately, 2.5 grams of a 5% solution of PVP-30 in Triton X-100 is prepared. To this solution the oxygen donor is added and to this combination the color enhancer is then added. This becomes the second portion of the test ink. The second portion of the test ink is then added to the first portion of the test ink.

The method of preparing the test sheet will now be explained. The test ink is printed on the entire test sheet excluding the negative monitor test area 18. Then, a polymer barrier is printed on the test ink. The polymer barrier is 10.0 grams of a 5% solution of PVP-30 in Triton X-100. Lastly, the positive test ink formulation as described above was printed in the positive monitor test area 16 on top of the polymer barrier. The test sheet prepared according to the aforementioned formulation produced acceptable results comparable to the results obtained with FDA-approved commercially available fecal occult blood test products.

The preferred printing technique heretofore utilized is a dual head offset press. On the first pass of the sheet through the press, the first head prints the test ink and the second head prints the graphics or legends. Then the sheet is sent through the press a second time. During this second pass through the press, the first head prints the polymer barrier and the positive test ink is printed by the second head. It should be appreciated that alternate printing equipment may be used and that the foregoing explanation is merely exemplary.

It should be pointed out that while the above formulation is given as a preferred commercial example, there are, of course, ranges for each of the ingredients. The range for each ingredient may vary by $+$ or $-15\%$ as long as there is an excess of oxygen donor. Although the amounts of ingredients may be changed, we believe that the specific sequence or order of combining the ingredients is of importance. Also, certain ingredients may be substituted for those listed in the above formulation without departing from the spirit and scope of the present invention.

A distinction should be made between the formulation of the present invention and the prior art. While the product described in the Patel, et al. application uses many of the same ingredients as described herein, there appears to be at least two significant differences. For example, the present invention utilizes about 40-60% of Triton X-100 as a bridge, or surfactant, or solubilizing agent whereas the Patel, et al. formula includes only a small percentage of that type of ingredient. In addition, whereas the present invention includes only a small amount of PVP, functioning as a moisture barrier, the PVP is the predominant ingredient, apparently constituting about 75% of the formulation of the Patel, et al. application. Thus, the mere presence of similar or identical ingredients in the prior art, without regard to their proportions and functions, may inaccurately suggest that the present formulation taken as a whole is a mere trivial variation of prior formulations.

In addition to the foregoing, we believe that the combination of foaming agent, solvent and encapsulator provides superior results insofar as stability and printability. The use of the fecal occult blood test product of the present invention will now be summarized. After the patient has completed a bowel movement, the test sheet is merely dropped into the toilet bowl. If the chromogen undergoes a color change within the specimen test area, the result of the test is considered positive for fecal occult blood. Conversely, the absence of a color change is considered as a negative result indicating the absence of fecal occult blood. The validity of the test is confirmed by a color change in the positive monitor test area and by the absence of a color change in the negative monitor test area. After the results of the test have been visually observed, the test sheet is disposed of by merely flushing the toilet bowl.

The foregoing is a complete description of a preferred embodiment of the present invention. The invention may be modified as to ingredients and amounts while taking into account the functions of the ingredients. The invention, therefore, should be limited only by the scope of the following claims.

What is claimed is:

1. A test sheet for the determination of the presence of a substance having peroxidase-like activity such as hemoglobin in an aqueous solution comprising:
    a sheet having a specimen test area, a positive monitor area and a negative monitor area, said sheet comprising an inert water insoluble matrix;
    said specimen test area having deposited thereon a first composition comprising at least one oxygen donor agent in a solvent comprising a surfactant to form a first solution and at least one chromogen reagent in a solvent comprising a surfactant, to form a second solution, the chromogen reagent capable of being oxidized by the oxygen donor in the presence of a substance having the peroxidase-like activity, to provide a visually observable change of color; said oxygen donor agent and said chromogen reagent of said first composition being inert relative to each other in the absence of both an aqueous solution and a substance in said aqueous solution having peroxidase-like activity,
    said first solution and said second solution being mixed together to form said first composition prior to being deposited on said specimen test area; and
    said positive monitor test area having deposited thereon said first composition and a second composition comprising a substance having peroxidase-like activity, said first composition being inert relative to said second composition in the absence of said aqueous solution.

2. The invention of claim 1 wherein the matrix is a sheet comprising fibers of cellulose.

3. The invention of claim 1 wherein the first composition further includes at least one water soluble polymer functioning as a moisture barrier for maintaining said chromogen reagent and said oxygen donor agent inert relative to each other in the absence of said aqueous solution.

4. The invention of claim 3 wherein the first composition includes a stabilizer to prevent premature interaction between said first composition and said second composition and the at least one chromogen reagent includes 3,3'5,5'-tetramethylbenzidine and wherein the at least one water soluble polymer includes polyvinlypyrrolidone.

5. The invention of claim 1 wherein said first composition includes a moisture barrier for maintaining said chromogen reagent and said oxygen donor agent inert relative to each other in the absence of said aqueous solution.

6. The invention of claim 1 wherein said second composition includes crystalline hemoglobin.

7. A test sheet adapted for contact with fluids containing biological samples, for detecting the presence of a substance having peroxidase-like activity, comprising:
    a sheet having a specimen test area and a positive monitor area, said sheet comprising fibers of cellulose serving as a matrix;
    said specimen test area having deposited thereon a first composition comprising:
    3,3',5,5'-tetramethylbenzidine in a solvent comprising a surfactant to form a first solution and capable of being oxidized by an oxygen donor in the presence of a substance having the peroxidase-like activity to provide a visually observable change of color,
    at least one oxygen donor agent in a solvent comprising a surfactant including cumene hydroperoxide to form a second solution; said oxygen donor agent and 3,3',5,5'-tetramethylbenzidine of said first composition being inert relative to each other in the absence of both an aqueous solution and a substance in said aqueous solution having peroxidase-like activity,
    said first solution and said second solution being mixed together to form said first composition prior to being deposited on said specimen test area; and
    said positive monitor area including said first composition, a barrier applied to said first composition, and a second composition comprising a substance having the peroxidase-like activity.

8. The invention of claim 7 wherein the first composition further contains between about 10% to about 14% stabilizer by weight, to prevent premature interaction between said first composition and said second composition.

9. The invention of claim 7 wherein said cumene hydroperoxide is present in an amount from about 15% to about 25% by weight and said 3,3',5,5'-tetramethylbenzidine is present in an amount from about 1% to about 4% by weight.

10. The invention of claim 7 wherein said first composition include polyvinylpyrrolidone as a moisture barrier.

11. The invention of claim 7 wherein the first composition includes from about 3% to about 7% polyvinylpyrrolidone by weight.

12. The invention of claim 7 wherein said first composition includes a color enhancing agent.

13. The invention of claim 7 wherein said first composition includes from about 1% to about 3% by weight of a color enhancing agent.

14. The invention of claim 7 wherein said first composition includes alkylphenoxypolyethoxyethanol functioning as a surfactant.

15. The invention of claim 7 wherein said second composition comprises 1-5% by weight solution of crystalline hemoglobin dissolved in a solvent.

16. The invention of claim 7 wherein said first composition includes the following active ingredients in the following approximate proportions: one part 3,3', 5,5'-tetramethylbenzidine, one part color enhancer and ten parts cumene hydroperoxide.

* * * * *